(12) United States Patent
Busch et al.

(10) Patent No.: US 7,883,689 B2
(45) Date of Patent: Feb. 8, 2011

(54) INDUCED REMINERALISATION OF HUMAN TOOTH ENAMEL

(75) Inventors: Susanne Busch, Dresden (DE); Rüdiger Kniep, Langenfeld (DE)

(73) Assignee: Max-Planck-Gesellschaft zur Forderung der Wissenschaften e.V., Munich (DE)

( * ) Notice: Subject to any disclaimer, the term of this patent is extended or adjusted under 35 U.S.C. 154(b) by 164 days.

(21) Appl. No.: 10/515,509

(22) PCT Filed: May 23, 2003

(86) PCT No.: PCT/EP03/05430

§ 371 (c)(1),
(2), (4) Date: Nov. 24, 2004

(87) PCT Pub. No.: WO03/099234

PCT Pub. Date: Dec. 4, 2003

(65) Prior Publication Data

US 2005/0220724 A1    Oct. 6, 2005

(30) Foreign Application Priority Data

May 24, 2002   (DE)   .......................... 102 23 157 U (51) Int. Cl.
*A61K 8/00*   (2006.01)
*A61K 8/55*   (2006.01)
*A61K 8/21*   (2006.01)
*A61K 8/58*   (2006.01)

(52) U.S. Cl. .............................. 424/49; 424/51; 424/57; 424/601; 424/602; 433/217.1; 106/31.54

(58) Field of Classification Search ................... 424/49, 424/57

See application file for complete search history.

(56) References Cited

U.S. PATENT DOCUMENTS

| 4,083,955 | A | * | 4/1978 | Grabenstetter et al. | ......... 424/49 |
| 4,397,837 | A | * | 8/1983 | Raaf et al. | .................... 424/51 |
| 4,474,750 | A | * | 10/1984 | Gaffar et al. | .................. 424/49 |
| 6,010,684 | A | * | 1/2000 | Wiedemann | ................. 424/52 |
| 2003/0152528 | A1 | * | 8/2003 | Singh et al. | .................... 424/53 |

FOREIGN PATENT DOCUMENTS

| DE | 21 31 666 A | 2/1972 |
| DE | 21 36 666 | 2/1972 |
| DE | 23 50 548 | 4/1974 |
| DE | 23 50 548 A | 4/1974 |
| DE | 33 03 937 | * 6/1984 |
| DE | 33 03 937 A | 6/1984 |
| DE | 33 03 937 A1 | 6/1984 |
| WO | WO 94 10969 A | 5/1994 |
| WO | WO 94 10969 A1 | 5/1994 |
| WO | WO 98 10736 A | 3/1998 |
| WO | WO 98 10736 A1 | 3/1998 |

* cited by examiner

*Primary Examiner*—Frederick Krass
*Assistant Examiner*—Lezah W Roberts
(74) *Attorney, Agent, or Firm*—Rothwell, Figg, Ernst & Manbeck, P.C.

(57) ABSTRACT

The present application relates to the induced remineralization of human tooth enamel and in particular to the building up of apatite on tooth material.

13 Claims, 9 Drawing Sheets

INDUCED REMINERALISATION OF HUMAN TOOTH ENAMEL

CROSS REFERENCE TO RELATED APPLICATION

This application is a 35 U.S.C. §371 National Phase Entry Application from PCT/EP03/05430, filed May 23, 2003, and designating the U.S.

The present application relates to the induced remineralization of human tooth enamel and in particular the building up of apatite on tooth material.

Teeth are composite materials formed from apatite and proteins. They are very hard biomaterials based on calcium and phosphate. The tooth enamel, the outer layer of the crown of the tooth, is the hardest part of the tooth and contains no living cells. Tooth enamel consists of inorganic crystals, which have typical highly oriented arrangements. Tooth enamel is a tissue which, as soon as it is formed, remains unchanged almost for life, since the cells which are involved in the construction of the teeth die as soon as tooth formation is complete. Finished tooth enamel consists of approximately 95% by weight of apatite, approximately 3% by weight of proteins and lipids and approximately 2% by weight of water.

In order to avoid or to repair damage to teeth, in particular by caries, it has been attempted for a long time to employ remineralizing systems. It was initially attempted here to improve the condition of the teeth by application of calcium phosphate compounds. Such single-component systems in which it is attempted to apply tooth material which has already been previously prepared, for example apatite, hydroxyapatite or other calcium phosphate compounds, to the teeth are described, inter alia, in EP 0 666 730 B1 or WO 01/95863. The problem of such systems is that treating tooth material with calcium phosphate compounds does not lead to growth of apatite which is structurally similar to the tooth material, but rather to a mere addition of apatite crystals to the tooth material, the apatite crystals having a morphology which is completely different from the tooth material. No strengthening of the tooth enamel or permanent filling of lesions is thus brought about, since the apatite crystals added do not have sufficient similarity and adhesion to the natural tooth material.

It was furthermore attempted with two-component systems to obtain a remineralization of teeth, the systems customarily comprising a calcium phase and a phosphate phase. Two-component systems are described, for example, in WO 98/10736 and DE 33 03 937 A1. It is disadvantageous with the procedures described there that the method described in WO 98/10736 combines calcium and phosphate solutions before application such that a metastable solution is formed from which apatite should crystallize out on the tooth. The method does not allow localized treatment on the tooth, since the reagent is employed as a mouthwash or gel which is massaged in using a toothbrush. Furthermore, the composite nature of the native enamel is not taken into account, since no organic component is contained in the system. The formation of tooth enamel-like crystallites is accordingly improbable. DE 33 03 937 describes a process in which calcium and phosphate ions are applied separately to the tooth in succession by immersing this in a cap which contains the corresponding ions in a gelatin matrix. With a recommended time of action of only two minutes, it is not to be expected that really larger amounts of apatite can be formed on the tooth surface. It is not confirmed using image material that the newly formed apatite layer has enamel-like structures.

In further studies (S. Busch et al., Eur. J. Inorg. Chem. (1999), 1643-1653; S. Busch et al., Chem. Mater. 13 (2001), 3260-3271; S. Busch, Zahnärztliche Mitteilungen [Dental Communications] 91, No. 10 (2001), 34-38; R. Kniep et al., Angew. Chem. 108, No. 22 (1996), 2787-2791), the biomimetic morphogenesis of fluoroapatite gelatin composites was investigated. Biomimetic growth and self-organization of fluoro-apatite aggregates by means of diffusion in denatured collagen matrices were observed here. The fundamental principles of fluoroapatite formation in gelatin gels was investigated here by means of double diffusion experiments of calcium and phosphate solutions in a U-tube. These studies describe the formation of fluoroapatite beads within the gel used.

It was an object of the present application to provide a process with which defects on tooth material can be repaired by remineralization. It was a further object to cover tooth material with a protective apatite layer.

This object is achieved according to the invention by a process for the growth of apatite on tooth material, comprising the steps:

(i) application of a first gel which comprises gelatin and phosphate ions,
(ii) application of a second gel, the first layer of gel being covered with this second gel and
(iii) application of a medium containing calcium ions, a building up of apatite on the surface of the tooth material being caused.

BRIEF DESCRIPTION OF THE DRAWINGS

FIG. 4b is a SEM-micrograph showing the top view of the layer of FIG. 4a.

The invention relates in particular to the use
(i) of a first gel which comprises gelatin and phosphate ions,
(ii) of a second gel which is free of phosphate ions, the first layer of gel being covered with this second gel and
(iii) of a medium containing calcium ions, for the production of an agent or of a kit for the growth of apatite on tooth material.

According to the invention, it is surprisingly possible to achieve a real growth of tooth enamel-like material. A significant advantage consists in the fact that a high order of small apatite needles is obtained, which structurally have a great similarity to native tooth enamel. With appropriate substrate orientation, virtually no difference can be detected between apatite which has grown and original tooth material.

Further advantages of the invention are that a real growth of the fluoroapatite crystallites on the tooth substrate can be assumed, as the SEM images show. The Vickers hardness of this novel layer corresponds to that of natural enamel. Carrying out the individual steps is so simple that the remineralization of tooth enamel can in principle be carried out by the patient himself. The gel can be applied locally to the damaged sites and solidifies there. Since the warmed gel cools very rapidly, waiting times between the individual steps are barely necessary.

Since the softening temperature of the gel is somewhat above normal body temperature (38 to 42° C.), melting of the gel during the period of action is prevented. Uncontrolled mineralization can thus be avoided.

By addition of fluoride ions to the phosphate-containing gel, the resistance of the layer to acids can be increased.

According to the invention, it is possible by means of induced remineralization to regenerate tooth enamel defects. By the use of a two-layer gel which is solid at body temperature and can be applied locally to the affected site on the tooth, and by the use of a mouth rinsing as a medium containing calcium ions, mineralization conditions are created which bring about the formation of a tooth enamel-like substance which grows directly on the tooth. In the case of the previously published double-diffusion method, it was shown only that fluoroapatite which results by countercurrent diffusion of calcium and phosphate ions in a gelatin gel forms spherical aggregates whose organic proportion by weight corresponds to that of mature, human tooth enamel. The double-diffusion method, however, has neither opened up a possibility of making possible the remineralization of tooth enamel in man nor implied this possibility in any manner. The experimental setup employed in the double-diffusion method brings about the formation of small beads and does not allow the growth of uniform layers of apatite material on a substrate. This is only possible by means of the procedure according to the invention.

The invention can be applied, in particular, in man. It is possible here, for example, to cure relatively small carious defects by induced remineralization or to cover sensitive sites on the tooth with a protective apatite layer. The procedure for treatment here is preferably as follows: The carious site is initially painted with a thin layer of the phosphate-containing gel warmed to approximately 50° C. or this is applied with a suitable syringe, which can be warmed. The gel solidifies immediately on the surface of the tooth and is covered with the protective gel according to the same method. 1 to 3 times a day, an approximately 10-minute mouth rinsing is then carried out with the calcium solution. Between the rinsings, the tooth is covered with a suitable cap, which can be made of plastic or metal, such that the patient is not incapacitated and the remineralization can take place undisturbed. If many teeth are affected, the whole row of teeth can also be protected with a rail, such as is employed, for example, against odontoprisis. Every two days, the gel is changed, and at this opportunity the affected tooth is cleaned and disinfected.

According to the invention, initially a first gel is applied to the tooth material. This gel contains gelatin and phosphate ions and optionally further constituents. The content of gelatin in the first gel is preferably from at least 15% by weight, more preferably from 25% by weight, up to 40% by weight, more preferably up to 30% by weight. The gelatin, in particular, has a function in the development of the morphology of the apatite formed. It was surprisingly discovered that when using gelatin, an apatite material is deposited on the surface of the tooth material which has a great similarity with native tooth enamel. When using other organic matrices, however, other morphologies of the apatite crystallizates were observed, such that a building up of apatite on the surface of the tooth material, as desired according to the invention, does not occur.

Gelatine is a polypeptide which can be obtained, in particular, by hydrolysis of the collagen contained in the skin and bone of animals. Gelatine customarily has a molecular weight of 15,000 to over 250,000 g/mol and can be obtained from collagen under acidic or alkaline conditions. According to the invention, the following gelatins are preferably employed: Acid-hydrolyzed gelatin types (type A), e.g. prepared from pigskin or calfskin having a high Bloom value, e.g. 250 to 350 Bloom (the Bloom value is understood as meaning a parameter which characterizes the gel solidity, in general it is true that the higher the Bloom value, the higher the proportion of long-chain molecules in the gelatin and the higher the gel solidity).

Beside gelatin, which is contained for the formation of the desired morphology of the apatite and the building up on the surface of the tooth material, the first gel furthermore comprises phosphate ions. These phosphate ions represent a basic constituent of the apatite built up from calcium phosphate. The concentration of the phosphate ions in the first gel is preferably at least 0.01 mol/l, more preferably at least 0.05 mol/l, and up to 0.5 mol/l, more preferably up to 0.2 mol/l, and in particular 0.08 mol/l.

The first gel preferably has a softening temperature which lies above normal body temperature such that the gel is solid at body temperature. The softening temperature of the first gel preferably lies in the range from 38 to 45° C., more preferably from 38 to 42° C. The first gel is preferably applied in warmed form, for example warmed to 45 to 55° C. After applying, the gel cools and becomes solid.

According to the invention, a second gel, a so-called protective gel, is applied in a further step. The first gel layer, in particular, is covered with this second gel. The protective gel, which functions as a gel covering layer, surprisingly causes the mineralization, that is the formation of apatite, to take place mainly or exclusively on the surface of the tooth and not on the gel-liquid boundary layer. By means of the two-layer gel construction which is achieved in the process according to the invention, surprisingly a building up or growth of apatite on the tooth material and not a crystallization or formation of apatite spheres within the gel occurs, as is described in the prior art. Only by means of the two-layer construction is a practicable and technically useful remineralization of the teeth thus possible.

The pH and the gel concentrations of the second gel typically correspond to those which are indicated herein for the first gel. The second gel also preferably has a softening temperature of 38 to 45° C., in particular of 38 to 42° C. and is preferably applied warmed to 45 to 55° C.

In a third step, a medium containing calcium ions is finally applied. The medium containing calcium ions provides the basic structural material further needed for the formation of apatite, namely calcium ions. These calcium ions diffuse through the protective gel and the first gel layer as far as the surface of the tooth material and are deposited there as apatite. The concentration of the calcium ions in the medium containing calcium ions is preferably at least 0.01 mol/l, more preferably at least 0.05 mol/l, and up to 0.5 mol/l, more preferably up to 0.2 mol/l, and in particular 0.13 mol/l.

It was discovered that according to the invention surprisingly a uniform layer of apatite crystallites which are parallel or radial can be formed. Furthermore, this layer exhibits no peripheral gap or only a submicrometer-large peripheral gap to the native tooth material. The direction of growth of the apatite crystallites takes place perpendicular to the substrate, independently of the orientation of the enamel prisms, such that on suitable orientation of the enamel prisms the longitudinal orientation of the artificially grown crystals proceeds substantially identically to the crystals in the prisms. The order of magnitude of fusion crystals and grown fluoroapatite is identical. Within the layers, a tight and uniform packing can be observed. Furthermore, the apatite layer applied has a Vickers hardness which corresponds to that of the native tooth enamel. The apatite layers applied according to the invention in particular have a Vickers hardness in the range from 250 to 400 HV.

According to the invention, it is possible to apply apatite layers in any desired thickness, since the layer thickness achieved is dependent on the frequency of the change of gel. Per change of gel, up to now layer thicknesses of up to 1 μm can be achieved.

In a preferred embodiment, a gelatin-glycerol gel is employed as the first gel. The weight ratio of gelatin to glycerol is preferably 1:5 to 5:1 here, in particular 1:2 to 2:1. Glycerol has the effect that the softening point of the gel is raised above the normal human body temperature. The gel solidity achieved is necessary in order to obtain the two-layer system during the mineralization such that a specific, controlled crystal deposition is made possible. In a liquid gel, a spontaneous precipitation of finely crystalline material would occur, which does not grow on the tooth.

The first gel preferably furthermore contains fluoride ions. The fluoride can be added, for example, as sodium fluoride or ammonium fluoride. In this embodiment, fluorine-rich apatite or fluoroapatite can be grown on the surface of the tooth material. Fluoroapatite is, in particular, more acid-resistant than the carbonate-containing hydroxyapatite of the natural tooth enamel, the morphology of the layers of fluoroapatite forming nevertheless having a great similarity to native tooth enamel.

The growth rate of the apatite or fluoroapatite is determined, inter alia, by the pH of the first gel. Preferably, the first gel has a pH of 2.0 to 6.0, in particular of 4.0 to 6.0, more preferably of 5.0 to 5.5.

A significant feature of the present invention is the use of a protective gel as the second gel. The first gel layer containing phosphate ions is covered with this protective gel. By use of this protective gel layer, surprisingly the apatite formation takes place exclusively on the surface of the tooth material and a spontaneous crystallization of apatite crystallites or composite aggregates does not occur, such as is observed in the case of the procedures known in the prior art. In contrast to the investigations with double-diffusion chambers, a coating of tooth material surfaces can thus be obtained in a controlled manner. The second gel preferably contains no materials which are to be incorporated into the apatite, and is thus, in particular, free of phosphate ions, calcium ions and/or fluoride ions. Gelatine can likewise be employed for the formation of the second gel, a gelatin-glycerol gel being preferred. The second gel used can, however, also be another gel, e.g. selected from polysaccharides, for example agarose or carrageen, and also carboxymethylcellulose.

According to the invention, the tooth material coated with a first gel and protective gel is finally treated with a medium containing calcium. The medium containing calcium employed can be, for example, a solution containing calcium ions and/or a gel containing calcium ions. The medium containing calcium ions is preferably prepared here using a water-soluble salt containing calcium ions, for example from $CaCl_2$.

The medium containing calcium ions preferably has a pH of 6 to 8.

According to the invention, the two constituents of apatite, namely phosphate ions and calcium ions, are in each case separately supplied as an individual component, the calcium phosphate formation then only taking place on the tooth material surface.

In order to prevent a local overacidification on the mineralization front by means of the proton release during the apatite formation, the phosphate gel is preferably treated with a buffer system, preferably an acetic acid buffer or $\alpha,\alpha\alpha$-tris (hydroxymethyl)methyl-amine buffer.

Before the treatment with the first gel, the tooth material can be pretreated, in particular defatted, etched or/and rinsed. For example, for better efficacy the tooth surface can initially be defatted with ethanol and etched with phosphoric acid and subsequently rinsed with deionized water.

The process according to the invention is suitable, in particular, for the treatment of human teeth or tooth enamel. Carious defects can be treated here by remineralization or else the tooth material can also be covered prophylactically with a protective apatite or fluoroapatite layer. The apatite layers are formed both on tooth enamel and on dentine as a substrate.

The invention furthermore relates to a composition and/or a kit which, in particular, is suitable for the use described above and comprises a) a first gel which comprises gelatin and phosphate ions,
b) a second gel which is free of phosphate ions, and
c) a medium containing calcium ions.

The preferred embodiments of the first and second gel and of the medium containing calcium ions are as described above here.

The invention is further illustrated by the attached figures and the following examples.

FIGS. 1 to 6 show SEM-micrographs of apatite grown on tooth material.

EXAMPLES

Example 1

Step 1. Preparation of the Tooth Material

A human tooth (arbitrary) was separated from its root and the crown was sawn into disks approximately 0.5 mm wide, namely such that the longitudinal axis of the enamel prisms was orientated obliquely to the direction of the cut. The disks were immersed for 30 s in a 30% strength phosphoric acid solution, washed with deionized water and dried.

Step 2. Preparation of the Gel

A homogeneous gel whose pH was 5.0 was prepared at 80° C. with stirring from 8.56 g of gelatin, 8.24 g of 85% glycerol solution, 7.26 g of $H_2O$, 1.8 ml of 2N NaOH, 2.7 ml of 2N HAc, 13.8 mg of NaF and 236 mg of $Na_2HPO_4$. A further gel was prepared from 8.56 g of gelatin, 8.24 g of 85% glycerol solution and 11.76 g of $H_2O$. A 0.133 molar calcium solution was prepared from $CaCl_2$ salt.

Step 3. Induced Mineralization on the Tooth Surface

The surface of the tooth disks was painted with approximately 0.5 ml of the phosphate-containing gel. After its solidification, covering was carried out with approximately 0.5 ml of the additive-free gel. The tooth disk was inserted into a plastic tube closed on one side and stored at 37° C. in a calcium solution. The gel and the solution were renewed every 7 days, altogether 16×. For the appraisal of the layer grown, a fracture of the sample perpendicular to the cut surface was carried out in order to be able to measure the layer thickness. As the SEM-micrograph in FIG. 1 confirms, a uniform layer of elongated crystallites having a layer thickness of 7.2 μm is formed. This corresponds to a growth rate of approximately 450 nm/week.

Example 2

The procedure is carried out analogously to example 1, but the direction of the cut of the tooth disks was largely perpendicular to the longitudinal axis of the enamel prisms. Moreover, the sample was stored at 36° C. and exposed to the calcium solution for only 60 min daily. The gel was replaced every 2 days. The sample was investigated after 10 replacement cycles. The SEM-micrograph (FIG. 2) shows a uniform layer of crystals arranged in parallel, whose orientation and order of magnitude corresponds to that of the native enamel. A submicrometer-large peripheral gap can be detected. The layer thickness is 2.7 μm. This corresponds to a growth rate of 135 nm/day.

Example 3

Figure 1:
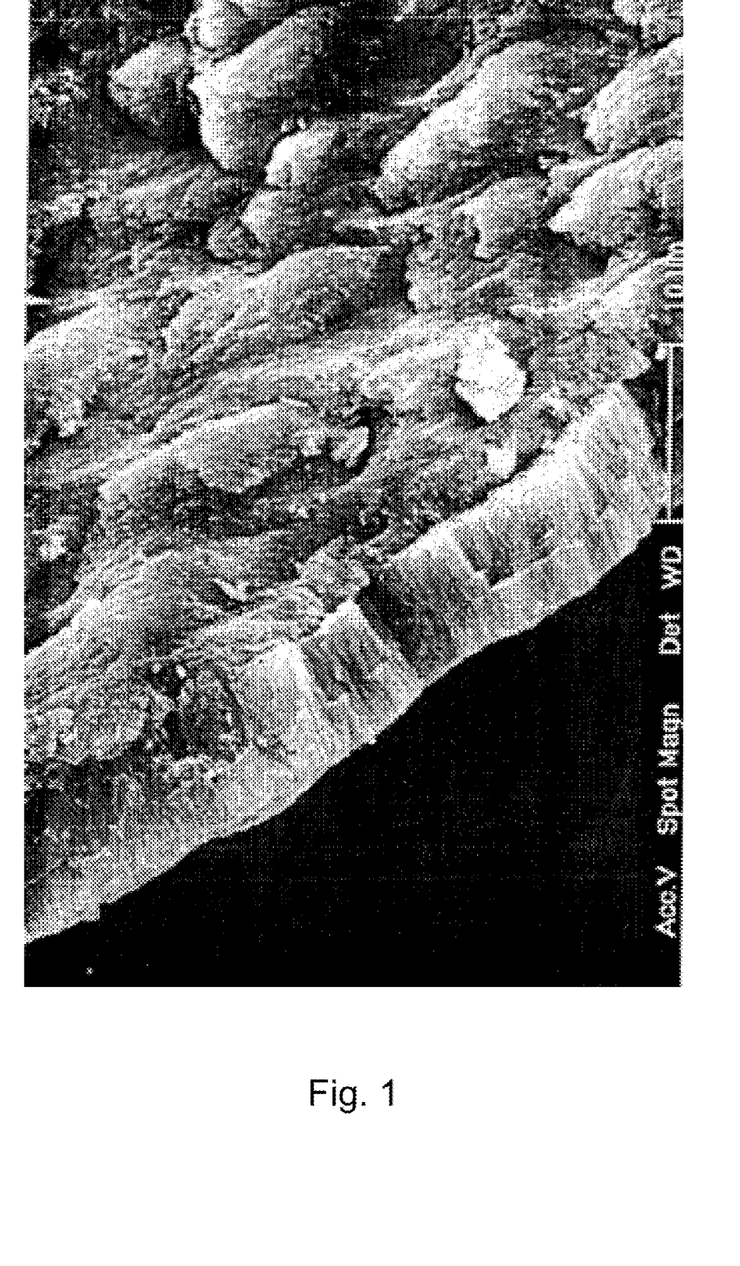
FIG. 1 is a SEM-micrograph of the surface of the tooth disks painted with approximately 0.5 ml of the phosphate-containing gel inserted into a plastic tube closed on one side and stored at 37° C. in calcium solution. The gel and the solution were renewed every 7 days, altogether 16 times.
Figure 2:
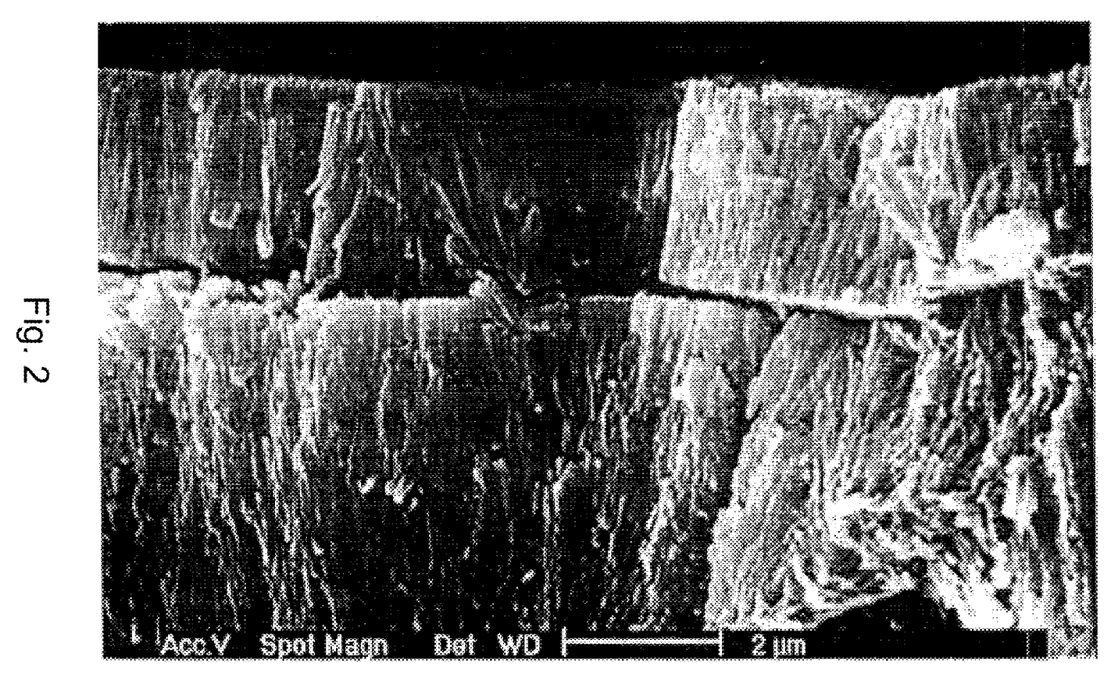
FIG. 2 is a SEM-micrograph of tooth disks cut largely perpendicular to the longitudinal axis of the enamel prisms painted with approximately 0.5 ml of the phosphate-containing gel inserted into a plastic tube closed on one side and stored at 36° C. and exposed to calcium solution for only 60 minutes daily. The gel was replaced every 2 days, altogether 10 times.
Figure 3A:
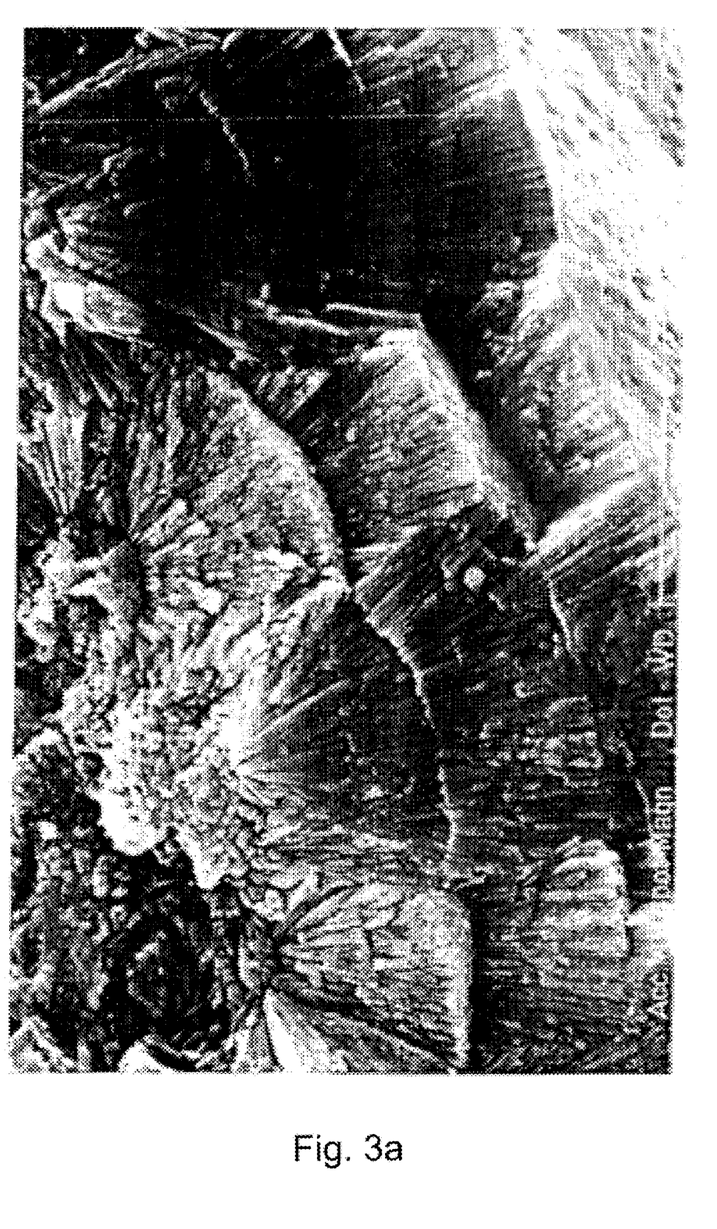
FIGS. 3a and 3b are SEM-micrographs of tooth disks cut largely parallel to the longitudinal axis of the enamel prisms painted with approximately 0.5 ml of the phosphate-containing gel inserted into a plastic tube closed on one side and stored at 37° C. in calcium solution. The gel was replaced every 2 days, altogether 36 times.
Figure 3B:
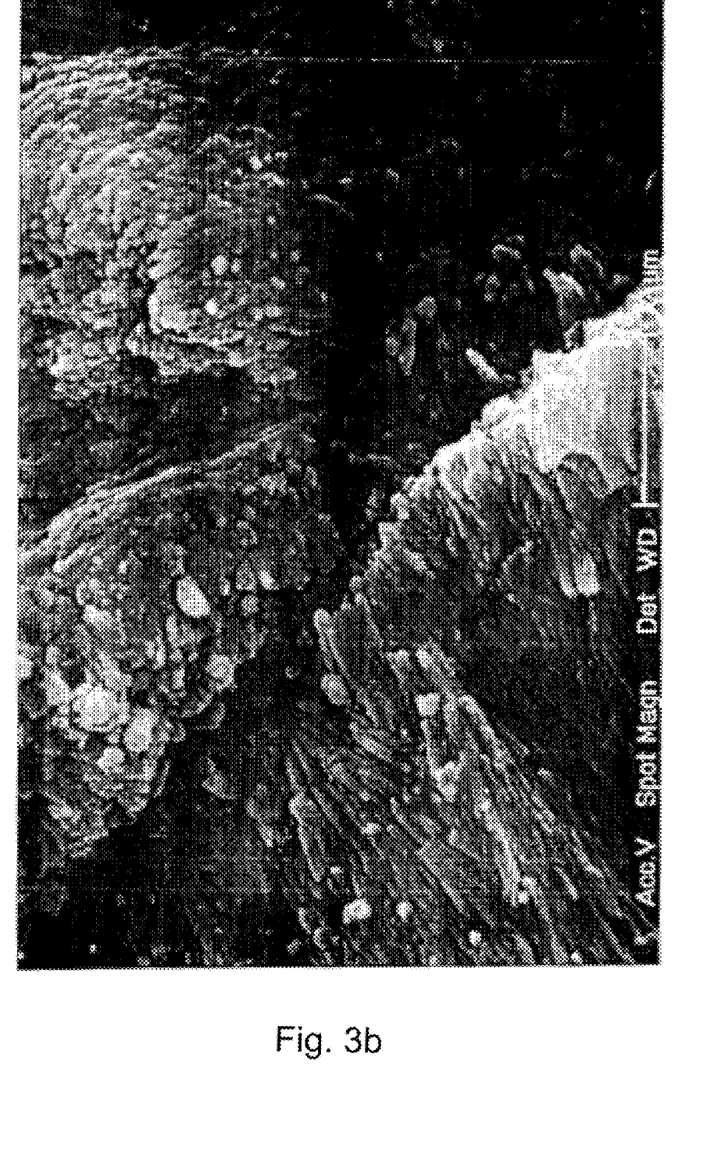

The tooth preparation was carried out analogously to example 1, but the direction of the cut of the disk was largely parallel to the longitudinal axis of the enamel prisms. The sample was stored at 37° C. and the replacement cycles correspond to example 2, but the gel was renewed 36× altogether. The SEM-micrograph FIG. 3a allows a uniform, 15 μm thick layer to be detected. Ray-like intergrown structures result here, which guarantee a good sealing of the native tooth surface. The peripheral gap to the tooth is minimal; very small, morphological peculiarities of the native surface are represented by the growing material (analogously to an impression). The size and morphology of enamel crystals and grown fluoroapatite are identical (FIG. 3b). The growth rate is approximately 210 nm/day.

Example 4

The procedure corresponds to example 2, but 755.2 mg were employed for the phosphate gel and the gel was replaced only 5×. Analogously to example 2, the SEM-micrograph (FIG. 4a) shows the corresponding orientation of enamel crystallites and grown fluoroapatite. The crystallites do not yet appear, however, to be completely matured. The layer thickness is 5 μm; this corresponds to a growth rate of 500 nm/day.

Example 5

Figure 4A:
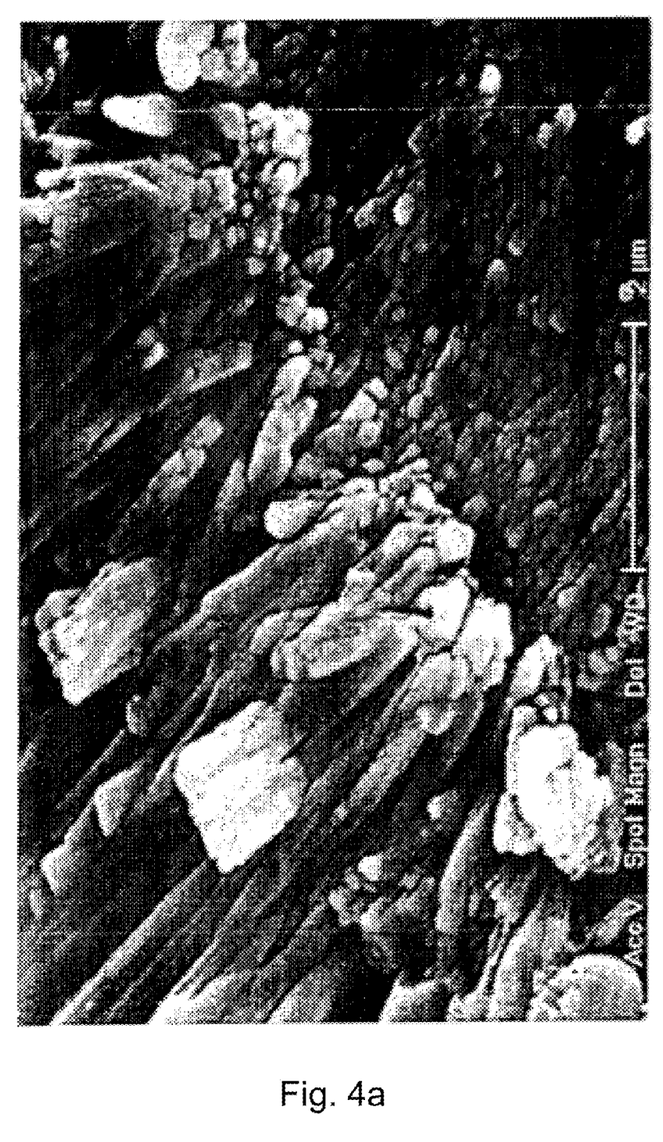
FIG. 4a is a SEM-micrograph of tooth disks cut largely perpendicular to the longitudinal axis of the enamel prisms painted with phosphate-containing gel inserted into a plastic tube closed on one side and stored at 36° C. and exposed to calcium solution for only 60 minutes daily. 755.2 mg were employed for the phosphate gel, which was replaced every 2 days, altogether 5 times.
Figure 4B:
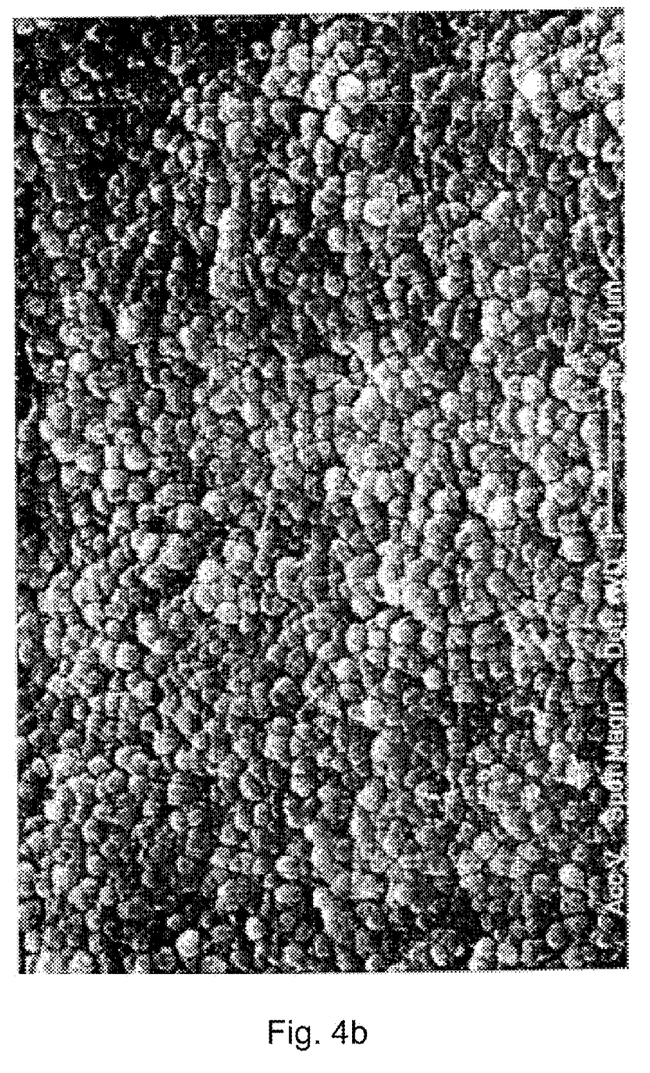
Figure 5:
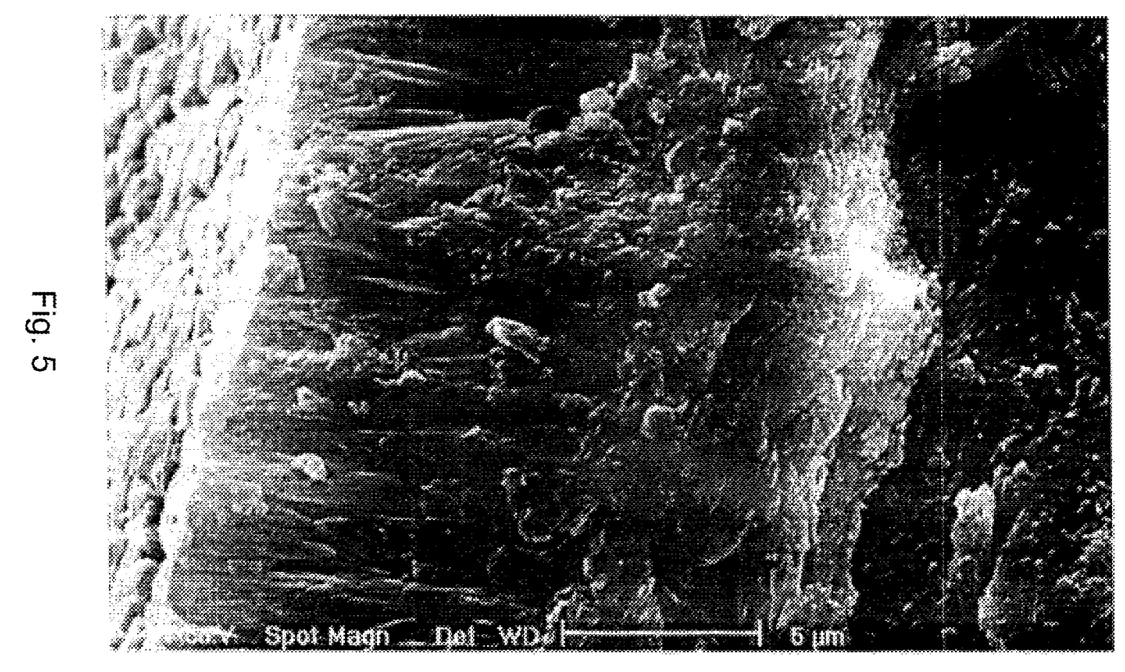
FIG. 5 is a SEM-micrograph of tooth disks cut largely perpendicular to the longitudinal axis of the enamel prisms painted with phosphate-containing gel inserted into a plastic tube closed on one side and stored at 36° C. and exposed to calcium solution for only 60 minutes daily. 755.2 mg were employed for the phosphate gel, which was replaced every 2 days, altogether 10 times.

The procedure corresponds to example 4a, but the direction of the cut was carried out parallel to the longitudinal axis of the enamel prisms and the sample was investigated only after 10 gel exchange cycles. At 9 μm, the layer is almost twice as thick as that from example 4 (cf. FIG. 5), which points to the linearity of the growth rate. It appears more mature than the layer in example 4. The lacking peripheral gap between native and grown material is clear. FIG. 4b shows the top view of this layer, which is morphologically largely representative of all layers.

Example 6

Figure 6A:
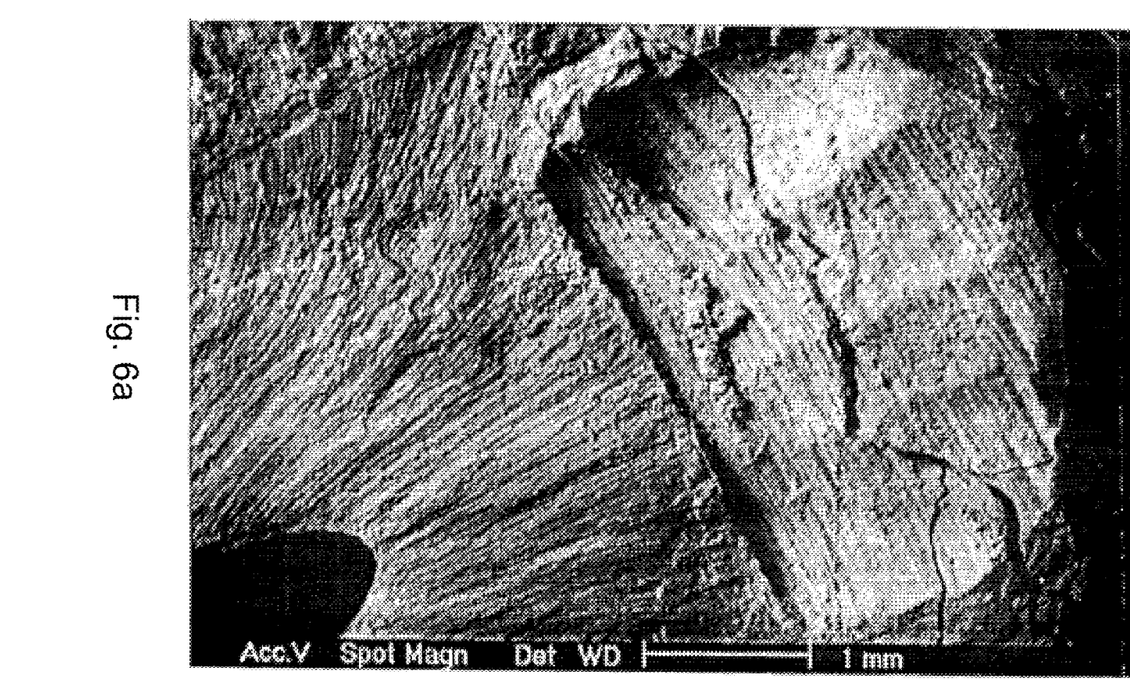
FIGS. 6a and 6b are SEM-micrographs of a cavity bored into the chewing surface of a premolar using after treatment.
Figure 6B:
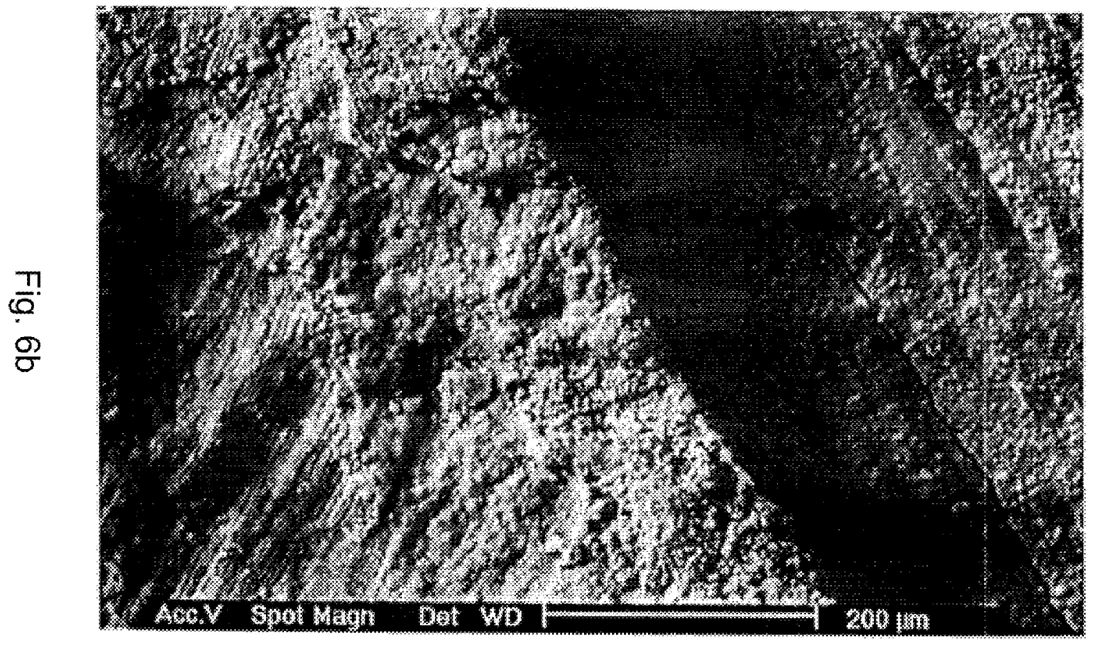

In order to adapt the synthesis conditions even more to the real problem in caries-related hard tooth tissue destruction, a cavity having the dimensions (H×W×L) 3×3×2 mm was bored into the chewing surface of a premolar. The further treatment corresponds to that of example 3. The calcium solution, however, contained 0.233 mol/l. The tooth sample was then fractured for the investigation such that the outline of the cavity can be detected. FIGS. 6a+b show clearly that both the cavity base and the side walls are covered.

All synthesis methods mentioned lead to firmly adhering fluoroapatite layers, which on the basis of the crystal morphology and arrangement have great similarity to native tooth enamel. The orientation of the growing crystallites basically runs perpendicularly to the surface of the substrate. By means of suitably frequent repetition of the replacement cycles, in principle arbitrarily thick layers can be produced.

The invention claimed is:

1. A method of repairing defective tooth material or of covering tooth material with a protective layer by growing apatite on tooth material comprising:
   (i) applying to the surface of at least one tooth a first layer comprising a first gel which comprises gelatin and phosphate ions,
   (ii) applying a second layer over said first layer wherein said second layer comprises a second gel which comprises gelatin and is free of phosphate ions, calcium ions and fluoride ions, and wherein the second layer acts as a protective layer and covers the first layer; and
   (iii) applying a third layer over said second layer wherein said third layer comprises a medium containing calcium ions.

2. The method of claim 1, wherein the first gel employed is a gelatin-glycerol gel.

3. The method of claim 1 wherein the first gel furthermore contains fluoride ions.

4. The method of claim 1, wherein the first gel has a pH of 2.0 to 6.0.

5. The method of claim 1, wherein the second gel is a gelatin-glycerol gel.

6. The method of claim 1, wherein the medium containing calcium ions employed is a solution containing calcium ions or a gel containing calcium ions.

7. The method of claim 1, wherein the medium containing calcium ions has a pH of 6 to 8.

8. The method of claim 1, wherein the tooth material is defatted, etched or/and rinsed before the application of the first gel.

9. The method of claim 1, wherein the tooth material is human teeth or/and tooth enamel.

10. The method of claim 1, wherein the components (i), (ii) and (iii) are intended for the treatment of carious defects by remineralization.

11. The method of claim 1, wherein the tooth material is covered with a protective apatite layer.

12. A process for the growth of apatite on tooth material, comprising the steps
(i) applying to the tooth material a first gel which comprises gelatin and phosphate ions,
(ii) applying a second gel which is free of phosphate ions, calcium ions, and fluoride ions, the first layer of gel being covered with this second gel wherein said second gel comprises gelatin, and
(iii) applying to the second gel a medium containing calcium ions, a building up of apatite on the surface of the tooth material thereby being caused.

13. A method of growing apatite on a tooth in an orientation and structure approximating that of natural tooth enamel comprising:
(i) applying to the surface of at least one tooth a first layer comprising a first gel which comprises gelatin and phosphate ions,
(ii) applying a second layer over said first layer wherein said second layer comprises a second gel which comprises gelatin and is free of phosphate ions, calcium ions, and fluoride ions, wherein the second layer acts as a protective layer and covers the first layer, and
(iii) applying a medium containing calcium ions to said second layer.

* * * * *